US009140683B2

(12) United States Patent
Cherian et al.

(10) Patent No.: US 9,140,683 B2
(45) Date of Patent: Sep. 22, 2015

(54) SINGLE CHIP HAVING THE CHEMICAL SENSOR AND ELECTRONICS ON THE SAME DIE

(75) Inventors: Suman Cherian, Singapore (SG); Olivier Le Neel, Singapore (SG)

(73) Assignee: STMicroelectronics Pte Ltd., Singapore (SG)

(*) Notice: Subject to any disclaimer, the term of this patent is extended or adjusted under 35 U.S.C. 154(b) by 407 days.

(21) Appl. No.: 13/285,894

(22) Filed: Oct. 31, 2011

(65) Prior Publication Data

US 2012/0171713 A1    Jul. 5, 2012

Related U.S. Application Data

(60) Provisional application No. 61/428,826, filed on Dec. 30, 2010.

(51) Int. Cl.
*G01N 33/00*    (2006.01)
*G01N 33/487*    (2006.01)

(52) U.S. Cl.
CPC ........... *G01N 33/48785* (2013.01); *Y02B 10/70* (2013.01); *Y10T 436/143333* (2015.01); *Y10T 436/144444* (2015.01); *Y10T 436/172307* (2015.01); *Y10T 436/184* (2015.01); *Y10T 436/19* (2015.01); *Y10T 436/204998* (2015.01); *Y10T 436/205831* (2015.01)

(58) Field of Classification Search
CPC ...................................................... G01N 27/00
USPC .......................................................... 73/23.2
See application file for complete search history.

(56) References Cited

U.S. PATENT DOCUMENTS

| 2,648,823 | A | 8/1953 | Kock et al. |
| 2,717,356 | A | 9/1955 | Foster |
| 2,735,934 | A | 2/1956 | Keizer et al. |
| 3,083,573 | A | 4/1963 | Shaw |
| 3,210,607 | A | 10/1965 | Flanagan |
| 3,323,084 | A | 5/1967 | Glanc |
| 3,500,243 | A | 3/1970 | Polin |
| 3,854,337 | A | 12/1974 | Moran et al. |

(Continued)

FOREIGN PATENT DOCUMENTS

| EP | 0 822 579 A1 | 2/1998 |
| EP | 1 324 382 A1 | 7/2003 |

(Continued)

OTHER PUBLICATIONS

Kraver et al. A mixed signal sensor interface microinstrument. Sensors and Actuators A 91 pp. 266-277 (2001).*

(Continued)

*Primary Examiner* — Hezron E Williams
*Assistant Examiner* — Mark A Shabman
(74) *Attorney, Agent, or Firm* — Seed IP Law Group PLLC

(57) ABSTRACT

A semiconductor die includes a chemical sensor, a digital to analog converter, and microcontroller formed therein. The chemical sensor detects the presence of a chemical and outputs an analog signal to the digital to analog converter. The analog to digital converter converts the analog signal to a digital signal. The analog to digital converter outputs the digital signal to the microcontroller. Microcontroller calculates a value of the concentration of the selected chemical.

13 Claims, 7 Drawing Sheets

(56) References Cited

U.S. PATENT DOCUMENTS

| | | | |
|---|---|---|---|
| 3,971,661 A | | 7/1976 | Lindberg et al. |
| 4,017,820 A | | 4/1977 | Ross |
| 4,217,623 A | | 8/1980 | Nishino et al. |
| 4,482,882 A | | 11/1984 | Lüder et al. |
| 4,500,940 A | | 2/1985 | Kuisma et al. |
| 4,532,016 A | | 7/1985 | Chambaz et al. |
| 4,733,370 A | | 3/1988 | Kitajima et al. |
| 4,739,380 A | * | 4/1988 | Lauks et al. ............... 257/253 |
| 4,761,710 A | | 8/1988 | Chen |
| 5,018,395 A | | 5/1991 | Hickox et al. |
| 5,204,541 A | | 4/1993 | Smayling et al. |
| 5,262,279 A | | 11/1993 | Tsang et al. |
| 5,522,980 A | | 6/1996 | Hobbs et al. |
| 5,640,013 A | | 6/1997 | Ishikawa et al. |
| 5,643,804 A | | 7/1997 | Arai et al. |
| 5,814,726 A | | 9/1998 | Mitter |
| 6,085,576 A | | 7/2000 | Sunshine et al. |
| 6,287,750 B1 | | 9/2001 | Sakurai |
| 6,412,919 B1 | | 7/2002 | Ghozeil et al. |
| 6,448,695 B2 | | 9/2002 | Milsom |
| 6,467,332 B1 | | 10/2002 | Bertschi et al. |
| 6,504,226 B1 | | 1/2003 | Bryant |
| 6,635,585 B1 | | 10/2003 | Khe et al. |
| 6,649,357 B2 | | 11/2003 | Bryan et al. |
| 6,806,553 B2 | | 10/2004 | Yashima et al. |
| 6,821,729 B2 | | 11/2004 | Ackley et al. |
| 6,883,364 B2 | * | 4/2005 | Sunshine et al. ............ 73/23.34 |
| 6,933,807 B2 | | 8/2005 | Marksteiner et al. |
| 7,071,073 B2 | | 7/2006 | Villa et al. |
| 7,189,314 B1 | * | 3/2007 | Pace et al. ................... 204/412 |
| 7,242,569 B2 | | 7/2007 | Hunt et al. |
| 7,294,536 B2 | | 11/2007 | Villa et al. |
| 7,364,896 B2 | | 4/2008 | Schembri |
| 7,368,312 B1 | | 5/2008 | Kranz et al. |
| 7,594,435 B2 | | 9/2009 | Sudo |
| 7,651,868 B2 | | 1/2010 | McDevitt et al. |
| 7,683,891 B2 | | 3/2010 | Tran |
| 7,733,319 B2 | | 6/2010 | Aiba |
| 8,079,256 B2 | | 12/2011 | Langenbacher et al. |
| 8,325,460 B2 | | 12/2012 | Park et al. |
| 8,363,379 B2 | | 1/2013 | Edelstein et al. |
| 2003/0062807 A1 | | 4/2003 | Takeuchi et al. |
| 2003/0201450 A1 | | 10/2003 | Yamazaki et al. |
| 2004/0172798 A1 | | 9/2004 | Ruby et al. |
| 2005/0087787 A1 | | 4/2005 | Ando |
| 2005/0208696 A1 | | 9/2005 | Villa et al. |
| 2006/0125489 A1 | | 6/2006 | Feucht et al. |
| 2006/0171098 A1 | | 8/2006 | Won |
| 2006/0197118 A1 | | 9/2006 | Migliorato et al. |
| 2006/0257286 A1 | | 11/2006 | Adams |
| 2007/0290235 A1 | * | 12/2007 | Lehmann et al. ............ 257/253 |
| 2010/0107739 A1 | | 5/2010 | Marra |
| 2010/0163410 A1 | | 7/2010 | Mastromatteo et al. |
| 2010/0170324 A1 | | 7/2010 | Mastromatteo et al. |
| 2011/0051309 A1 | | 3/2011 | Furukawa et al. |
| 2011/0146400 A1 | | 6/2011 | Humbert et al. |
| 2011/0179861 A1 | | 7/2011 | Grange et al. |
| 2011/0209524 A1 | | 9/2011 | Ziglioli et al. |
| 2011/0318840 A1 | | 12/2011 | Ziglioli et al. |
| 2012/0168882 A1 | | 7/2012 | Cherian et al. |
| 2013/0207673 A1 | | 8/2013 | Tondokoro et al. |

FOREIGN PATENT DOCUMENTS

| | | |
|---|---|---|
| EP | 1 403 383 A1 | 3/2004 |
| JP | 4-364014 A | 12/1992 |
| WO | 2010/006877 A1 | 1/2010 |
| WO | 2011/085931 A1 | 7/2011 |

OTHER PUBLICATIONS

Cherian et al., "Chemical Sensor With Replaceable Sample Collection Chip," U.S. Appl. No. 13/285,867, filed Oct. 31, 2011, 39 pages.

Cherian et al., "Integrated Chemical Sensor," U.S. Appl. No. 13/285,911, filed Oct. 31, 2011, 56 pages.

Hwang et al., "CMOS VLSI Potentiostat for Portable Environmental Sensing Applications," IEEE Sensors Journal 10(4):820-821, Apr. 2010.

Schienle et al., "A Fully Electronic DNA Sensor With 128 Positions and In-Pixel A/D Conversion," IEEE Journal of Solid-State Circuits 39(12):2438-2445, Dec. 2004.

Turner et al., "A CMOS Potentiostat for Amperometric Chemical Sensors," IEEE Journal of Solid-State Circuits, SC-22(3):473-478, Jun. 1987.

Yang et al., "Amperometric Electrochemical Microsystem for a Miniaturized Protein Biosensor Array," IEEE Transactions on Biomedical Circuits and Systems 3(3):160-168, Jun. 2009.

Zhang et al., "Electrochemical Array Microsystem with Integrated Potentiostat," IEEE Sensors, pp. 385-388, 2005.

Benetti et al., "Chemical Sensor Based on Thin Film Bulk Acoustic Wave Resonator (TFBAR)," Proceedings of the 10th Italian Conference on Sensors and Microsystems, Firenze, Italy, pp. 326-331, Feb. 15-17, 2005.

D'amico et al., "Olfactometric Apparatus Based on Oscillating Crystal Sensors Functionalised with Tetrapyrrolic Macrocycles and Provided with Electronics for Conditioning and Reading the Signals, Communicationg with a PC, Managing Through a Software and Analysis and Displaying the Data," Italian Patent Application No. RM2001A000455, filed Jul. 26, 2001, 20 pages w/ English translation.

Matsumoto et al., "Influence of Underlayer Materials on Preferred Orientations of Sputter-Deposited AlN/Mo Bilayers for Film Bulk Acoustic Wave Resonators," Japanese Journal of Applied Physics 43(12):8219-8222, 2004.

Richter et al., "A High Performance Silicon Micropump for Fuel Handling in DMFC Systems," proceedings of the Fuel Cell Seminar, Miami Beach, FL, USA, pp. 272-275, Nov. 3-7, 2003.

Rosenbaum, "Bulk Acoustic Wave Theory and Devices," Boston, MA: Artech House, 1988, 7 pages.

Boser, "Capacitive Sensor Interfaces," Berkeley Sensor & Actuator Center, Department of Electrical Engineering and Computer Sciences, University of California, Berkeley, California, 40 pages, 1996.

Dokmeci et al., "A High-Sensitivity Polyimide Capacitive Relative Humidity Sensor for Monitoring Anodically Bonded Hermetic Micropackages," Journal of Microelectromechanical Systems 10(2):197-204, 2001.

Ford, "The Effect of Humidity on the Calibration of Precision Air Capacitors," Proceedings of the IEEE—Part III: Radio and Communication Engineering 96(39):13-16, 1949.

Hautefeuille et al., "A MEMS-based wireless multisensor module for environmental monitoring," Microelectronics Reliability 48:906-910, 2008.

Hautefeuille et al., "Development of a Microelectromechanical System (MEMS)-Based Multisensor Platform for Environmental Monitoring," Micromachines 2:410-430, 2011.

Holmberg, "Automatic Balancing of Linear AC Bridge Circuits for Capacitive Sensor Elements," IEEE Transactions on Instrumentation and Measurement, 44(3):803-805, Jun. 1995.

Hunter et al., "Smart Sensor Systems," The Electrochemical Society Interface, pp. 29-34, 2010.

Laconte et al., "High-Sensitivity Capacitive Humidity Sensor Using 3-layer Patterned Polyimide Sensing Film," Sensors, 2003, Proceedings of the IEEE, pp. 372-377.

Safari et al., "Ferroelectric Ceramics: Processing, Properties & Applications," URL=http://www.rci.rutgers.edu/~ecerg/projects/ferroelectric.html, 38 pages, last modified Aug. 28, 2000.

Sharma et al., "Integration of Precision Passive Components on Silicon for Performance Improvements and Miniaturization," 2nd Electronics Systemintegration Technology Conference, University of Greenwich, London, United Kingdom, Sep. 1-4, 2008, pp. 485-490.

St. Onge et al., "Design of Precision Capacitors for Analog Applications," IEEE Transactions on Components, Hybrids, and Manufacturing Technology, 15(6):1064-1071, Dec. 1992.

* cited by examiner

SINGLE CHIP HAVING THE CHEMICAL SENSOR AND ELECTRONICS ON THE SAME DIE

CROSS-REFERENCE TO RELATED APPLICATION

This application claims the benefit under 35 U.S.C. §119 (e) of U.S. Provisional Patent Application No. 61/428,826 filed Dec. 30, 2010 and is incorporated herein by reference in its entirety.

BACKGROUND

1. Technical Field

The present disclosure relates to a chemical sensor formed in a semiconductor die.

2. Description of the Related Art

Chemical sensors are used in a variety of applications. Chemical sensors are used in medical applications, industrial applications, automotive applications, security applications, and domestic applications. Some examples of chemical sensors are blood glucose sensors, carbon dioxide detectors, automobile exhaust emission monitors, radon detectors, carbon monoxide detectors, explosives detectors, and a large variety of other applications.

In the past, many chemical sensors have been large and relatively expensive. Many chemical sensors include discrete sensing elements and circuit components formed separately from each other. Such systems can be bulky and expensive to manufacture.

BRIEF SUMMARY

One embodiment is a chemical detection device formed in a single semiconductor die. The semiconductor die includes a chemical sensor, an analog to digital converter, and a microcontroller. The chemical sensor outputs an analog signal to the digital to analog converter. The analog signal varies according to the concentration of the selected chemical in the environment surrounding the semiconductor die. The analog to digital converter converts the analog signal to a digital signal. The analog to digital converter outputs the digital signal to the microcontroller. The microcontroller calculates the concentration of the selected chemical based on the digital signal.

DETAILED DESCRIPTION

Figure 1:
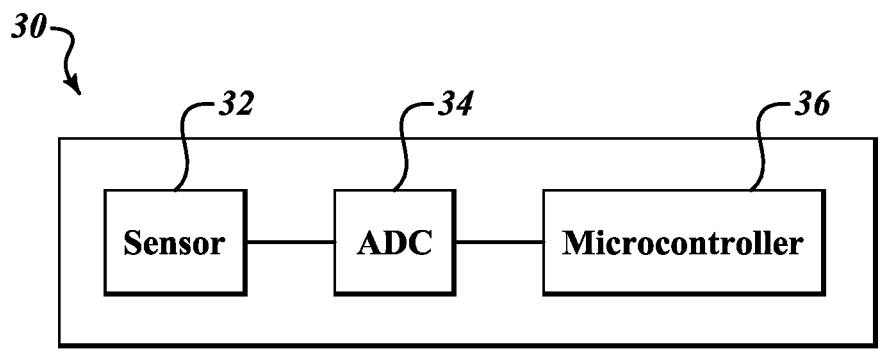
FIG. 1 is block diagram of a semiconductor die according to one embodiment.

FIG. 1 illustrates a single semiconductor die 30 according to one embodiment. The semiconductor die 30 includes a chemical sensor 32, an analog to digital converter 34, and a microcontroller 36. The analog-to-digital converter 34 is coupled to the chemical sensor 32. The microcontroller 36 is coupled to the analog-to-digital converter 34.

The chemical sensor 32 is configured to detect the presence of a selected chemical. The chemical sensor 32 outputs an analog signal indicative of the presence of the selected chemical to the analog-to-digital converter 34. The analog-to-digital converter 34 converts the analog signal to a digital signal. The analog-to-digital converter 34 then outputs a digital signal to the microcontroller 36. The microcontroller 36 receives the digital signal and computes or estimates a value of the concentration of the selected chemical.

The chemical sensor 32 can be designed to detect one or more selected chemicals according to a specific application of the chemical sensor 32. The chemical sensor 32 can be used in medical applications such as blood glucose testing, cholesterol testing, testing for blood gasses, testing for cancer markers, electrolytes, drugs, DNA, RNA, or any other suitable medical application. The design of the chemical sensor 32 is based on the desired application of the chemical sensor 32. In industrial applications the chemical sensor 32 can be designed to detect arsenic, lead, fluorides, volatile organic compounds, mercury, or any other suitable selected chemical, compound or substance. In environmental applications, the chemical sensor 32 can be designed to detect microorganisms, organic compounds, particulates in the water such as arsenic, mercury, cyanide, or other suitable particulates. The chemical sensor 32 can be configured to detect carbon dioxide in the air, nitrous oxide, hydrogen sulfide, HCN, or other particulates or chemicals in the air. In automotive applications the chemical sensor 32 is configured to detect carbon dioxide, carbon monoxide, nitrous oxide, or other particulates in the exhaust system of an automobile. The chemical sensor 32 can be used in a large variety of applications extending beyond what has been specifically mentioned above in light of the present disclosure.

Because the chemical sensor 32, the analog-to-digital converter 34, and the microcontroller 36 are formed in a single semiconductor die 30, a chemical detection system according to one embodiment is implemented fully integrated and inexpensively. In one embodiment, the semiconductor die 30 includes a monocrystalline silicon substrate (see FIG. 7). The microcontroller 36 and the analog-to-digital converter 34 are formed from transistors formed on the monocrystalline silicon substrate. In one embodiment, the chemical sensor 32 is formed on a dielectric layer of the semiconductor die 30. A portion of the chemical sensor 32 is on top of the semiconductor die 30 and exposed to the local environment. In one embodiment, the chemical sensor 32 includes a reactant such as an enzyme, a catalyst, or other compounds or substances configured to react with the selected chemical. The particular type of reactant used is based in part on the selected chemical. For a particular selected chemical, one reactant will be used, for another selected chemical, a different reactant can be used. A hardening or an adhesive agent may be placed on top of the reactant in order to anchor the reactant to the semiconductor die 30.

Use of the phrase "on the substrate" in this application is intended to be meant in the broadest sense of the word "on." As is well known in the art, when a transistor is formed on a silicon substrate, one or more portions of the transistor may be considered to be "in the substrate" while other portions of the transistor are above the substrate and may be referred to as being "on the substrate." In order to avoid confusion between use of the terms "on" and "in," the term "on" is used herein in the broadest sense of the word with respect to the formation of structures in an integrated circuit, and is broad enough to include structures which are in the silicon substrate, above the silicon substrate, overlying the substrate, on top of the substrate, and other equivalent locations in the formation of an integrated circuit. Thus, the chemical sensor, the microcontroller, the analog-to-digital converter, and other components which are in the same integrated circuit substrate are all described herein with the broad term as being formed on the substrate.

In one embodiment the microcontroller 36 stores a calibration table in memory. The calibration table stored in the microcontroller 36 is specific to the type of chemical sensor 32 formed in the semiconductor die 30. When the microcontroller 36 receives the digital signal from the analog to digital converter 38 the microcontroller 36 compares the digital signal to a calibration table as one step in computing the value of the concentration of the selected chemical. The memory of the microcontroller 36 can be programmed with calibration table according to the selected chemical. The calibration table can be updated or replaced if a more accurate calibration data is been developed. According to another embodiment, a conversion curve or conversion database is stored in the memory of the microcontroller 36. A conversion curve is a simple series of data points in which the value of the analog signal represents the x-axis and the concentration of the chemical of interest represents the y-axis. Thus, when the microcontroller 36 receives the digital data from the analog-to-digital converter, a simple comparison to the conversion curve outputs the relative concentration of the selected chemical. For some types of chemical sensing circuits, a conversion curve, sometimes termed a calibration curve, is a preferred tool for assistance in computing the concentration of the selected chemical. In other instances, a full conversion table, a calibration table, is preferred. For example, in many instances, the value of the digital data corresponding to the sensed chemical may be only one of the data points in determining the concentration of the selected chemical. Other ambient conditions may be sensed in order to accurately determine the concentration, such as the humidity, the temperature, the pH of the moisture content, and other factors. Thus, in many instances the conversion table may have different values for the conversion depending on the temperature of the sensor, the humidity of the sensor, and other factors. Thus, the conversion table may include a plurality of separate tables, one for each temperature or temperature range, and again, depending on the selected chemical to be sensed and whether or not the sensing varies according to temperature. There are a number of well-known techniques for converting an analog signal representative of the presence of a selected chemical to a data value indicative of the concentration of that selected chemical.

In one embodiment, the concentration of the chemical is not as important as the presence of the chemical or that the chemical is above a selected threshold. For example, in some embodiments, the mere presence of a particular chemical, such as carbon monoxide, certain types of blood cells, is sufficient to indicate the test is positive as compared to a negative. Accordingly, in some embodiments, the chemical sensor will output a signal indicating that the chemical has been sensed as present, and this alone is sufficient for purposes of the particular product. Thus, in this embodiment, the output signal is whether the selected chemical is present or not present, rather than providing a selected concentration of the particular chemical. In other embodiments, the signal is output if the selected chemical is above a threshold. For example, it may be desired to know whether or not carbon monoxide is above a selected threshold level in a particular environment. In such situations, the sensor will detect the presence of carbon monoxide and if it is determined to be below a selected threshold, then no signal is output. If, on the other hand, the presence of the carbon monoxide is above a selected threshold value, then a separate signal is output, such as an alarm signal, to indicate that the carbon monoxide in the local environment has exceeded a desired level and safety precautions should be taken. Thus, in this embodiment, the chemical sensor integrated with the semiconductor die is a threshold sensor outputting a signal that the chemical is above a selected threshold, rather than providing the exact number of the concentration of that particular chemical. Of course, the microcontroller 36 can compute or estimate the value of the concentration or it if is above a selected threshold of the selected chemical through any number of suitable ways which are equivalent to and interchangeable with each other in light of the present disclosure.

Metal interconnection layers in the semiconductor die 30 connect the analog-to-digital converter 34 to the chemical sensor 32. The metal interconnections also connect the microcontroller 36 to the analog-to-digital converter 34. Thus, in one embodiment, a chemical detection system is fully contained in a single semiconductor die 30.

In the embodiment of FIG. 1, the chemical sensor 32 is coupled to the analog-to-digital converter by one, or in some cases two electrical lines. Similarly, the analog-to-digital converter 34 is coupled to the microcomputer 36 by one or in some cases two signal lines. In the event there is only a single signal line between the components 32, 34 and 36, the circuits are coupled to an appropriate common ground provided on the semiconductor die. In the event there is only a single line between the analog-to-digital converter 34 and the microcontroller 36, the digital data is sent in series, usually a clocked rate from the analog-to-digital converter 34 to the microcontroller 36. Thus, an 8-bit or a 16-bit number can be sent as serial data on a single line according to a common control clock between the analog-to-digital converter 34 and the microcontroller 36.

Because the chemical detection system is completely contained in a single semiconductor die 30, the system can be manufactured relatively inexpensively. The chemical detection system fully integrated and completely contained in single semiconductor die 30 will also be very small. Because the semiconductor die 30 is small, it can be placed in unobtrusive locations. Because the chemical sensor 32 is located on the same die as the analog-to-digital converter 34, there is very little signal loss between the chemical sensor 32 and the analog-to-digital converter 34. There will be less attenuation and distortion in the analog signal that comes from the chemical sensor 32 and is received by the analog-to-digital converter 34. This allows for a more accurate conversion of the analog signal to the digital signal by the analog-to-digital converter 34. With a more accurate conversion to the digital signal, the microcontroller 36 can make a more accurate estimation or computation of the value of the concentration of the selected chemical.

The realization by the inventors that the microcontroller can be on the same die as the chemical sensor is a significant advance over the prior art with respect to obtaining accurate chemical analysis with small sample sizes. In the prior art in which the chemical sensor was on a separate semiconductor die than the microcomputer, an electrical signal had to pass from the sensor to the microcomputer in order for the data to be analyzed. This required some type of electrical connection outside of the semiconductor die between the two components, the chemical sensor on the one hand and the microcomputer on the other hand. In order to send an electrical signal on a separate wire, a large signal was required in order to assure it had a high enough amplitude to be transmitted along the wire. This required a large sample size of the chemical to be sensed. In addition, all electrical connections induce noise into the signal and an exposed wire is also susceptible to noise from multiple sources. Accordingly, such connections are very susceptible to noise from multiple sources. The signal had to be substantially larger than the noise so as to have a high signal-to-noise ratio. If the signal has approximately the same amplitude as the noise in the system, then it is difficult or virtually impossible to separate the signal from the noise in properly sensing the chemical at the microcomputer.

Having the chemical sensor on the same semiconductor die as the microcontroller, with all of them in the same integrated circuit, overcomes a number of problems in the prior art. A first advantage is that the pathway that the signal must travel is much shorter. In the case of the present invention, the signal path from the chemical sensor to the microcomputer is approximately the vertical height of the structure above the die, which is a very short signal path. The microcomputer has a number of electrical components located approximately at the surface of the die, while the chemical sensor will be separated therefrom by two or more insulating layers, but in many cases will be positioned directly above the main microcomputer components. Accordingly, the signal path is very short, usually in the range of 3,000 Å to 7,000 Å. A further benefit is that the signal path can be very low resistivity. For example, the electrical connections from the chemical sensor to the microcomputer can all be made in a highly conductive copper interconnect, or in some cases aluminum. Accordingly, the electrical connections from the chemical sensor to the microcomputer will be of a low resistivity metal and thus a very low amplitude signal is carried with very low resistance from the chemical sensor to the microcontroller 36. A yet further advantage is that the signal layers inside of the semiconductor die are not as susceptible to noise as signal paths which must leave the die. Within the semiconductor die, the electrical connections are made by deposited layers of metal over insulators, and thus there is little chance for noise to affect the interconnection points. In addition, the metal line carrying the signal is not exposed outside of the die, and thus is generally immune to outside noises. Therefore, the interconnection points between the chemical sensor and the microcontroller are all carried on inside the die as well as the line itself being contained within the die, and therefore the three main locations in which noise may enter the system are all contained in a very compact space inside the die and are made of connections of the type which are highly immune to noise as compared to signal connections which travel on terminals connected into and out of the semiconductor die.

Similar advantages are also obtained when the analog-to-digital converter and the chemical sensor are on the same die and the microcomputer 36 is on a different semiconductor die, as explained later herein.

A significant advantage of having all components on the same die is the increased sensitivity of the device with very small samples of the chemical to be sensed. As one example, the sensing of blood glucose today for a diabetes test usually requires a droplet of blood of a size in excess of one ml. With the present chemical sensor on the same integrated die as the analog-to-digital converter 34 and the microcomputer 36, a picoliter of blood, which is nothing more than a small fleck of blood, is acceptable for sampling the blood glucose. Similarly, very small quantities of other chemicals can be sensed, such as a few atoms of carbon monoxide, very small concentrations of lead in the water, and other chemicals having a concentration lower than parts per trillion. For example, chemicals having concentrations in the environment in the range of one quadrillion or one quatillion can be sensed because of the immunity to noise which the present circuit enjoys, as well as the low resistivity connections and other benefits that can be obtained by having all the sensors on a single integrated circuit with the microcomputer.

A further advantage is that each of the components, the sensor, the analog-to-digital converter, and the microcomputer will all be assured of having the same common ground, since all are electrically connected to the same semiconductor substrate. One of the problems in the prior art is that the actual ground voltage may fluctuate somewhat from one chip to the next, and changes in the precise ground voltage is a frequent source of noise in measuring very small signal propagations. Thus, the benefit of having a single integrated circuit with a common ground for all components thereon provides a further advantage in being able to sense small signal values and also keeping noise to a low value.

In one embodiment, the chemical sensor 32 is a reusable chemical sensor. The chemical sensor 32 can be used to test for the selected chemical multiple times. In one embodiment, the chemical sensor must be sterilized or cleaned after each test. In one embodiment, the chemical sensor 32 is used continuously to monitor the presence of the selected chemical.

Figure 2:
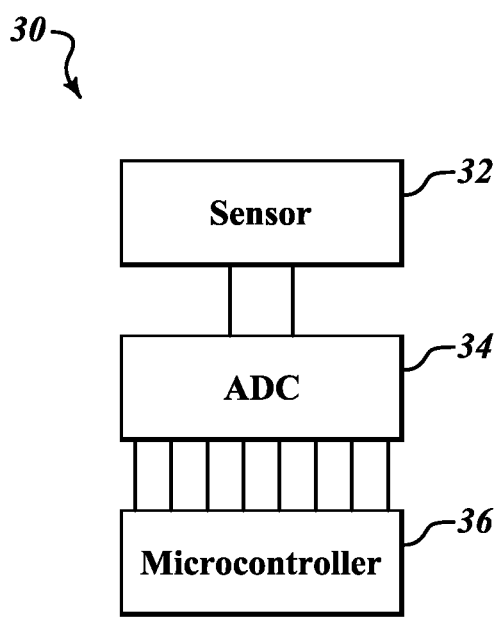
FIG. 2 is a block diagram of a semiconductor die according to a further embodiment.

Further details of the specific manufacture of chemical sensors can be found in copending U.S. patent application Ser. Nos. 13/016,086, 13/170,058, 13/285,867, and 13/285,911, all of which are incorporated by reference in their entireties. FIG. 2 is a block diagram of a semiconductor die 30 according to one embodiment. As in FIG. 1, a chemical sensor 32 is connected to an analog-to-digital converter 34. The analog-to-digital converter 34 is coupled to the microcontroller 36. The microcontroller 36 is coupled to the analog-to-digital converter 34 by a plurality of connections in parallel. In practice, there may be sixteen or more connections between the analog-to-digital converter 34 and the microcontroller 36. The analog-to-digital converter 34 will output a digital signal having a certain amount of bits on a multiline bus. In one embodiment, the analog-to-digital converter is an 8-bit analog-to-digital converter. In other embodiments, the analog-to-digital converter 34 may be a 4-bit, 16-bit, or 20-bit analog-to-digital converter. As the number of bits increases, so does the number of connections between the analog-to-digital converter 34 and the microcontroller 36. The sensor 32, the analog-to-digital converter 34, and the microcontroller 36 illustrated in FIG. 2 perform the same functions as described in relation to the semiconductor die 30 of FIG. 1.

Figure 3:
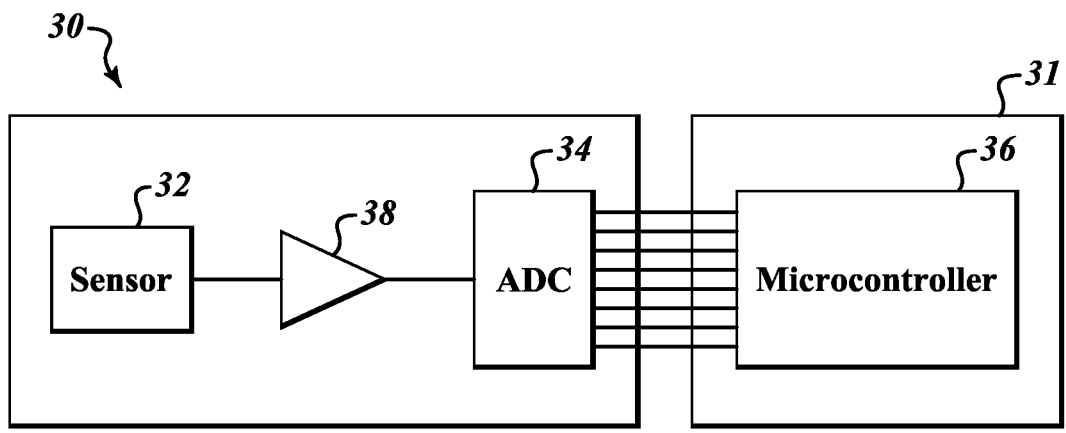
FIG. 3 is a block diagram of a semiconductor die including a signal amplifier according to one embodiment.

FIG. 3 is a block diagram of a semiconductor die 30 according to one embodiment. An amplifier 38 is coupled between the sensor 32 and the analog-to-digital converter 34. In one embodiment, the amplifier 38 receives the analog signal from the sensor 32. The amplifier 38 then amplifies the analog signal and outputs the analog signal to the analog-to-digital converter 34. Such an amplified signal allows for a more reliable and easy conversion of the analog signal to the digital signal by the analog-to-digital converter 34.

The amplifier 38 may also control the sensor 32. The amplifier 38 may be configured to apply a voltage to one or more electrodes of the chemical sensor 32. The amplifier 38 may maintain the voltages on electrodes of the chemical sensor 32. The amplifier 38 may also monitor the voltage on electrodes of the sensor 32. The amplifier 38 may receive a voltage signal from the sensor 32. The amplifier 38 may also receive a voltage signal from the chemical sensor 32. Thus, the analog signal output by the chemical sensor 32 may be a voltage signal or a current signal.

In one embodiment, the amplifier 38 includes a potentiostat. The potentiostat may include a control part and an amplification part. The control part may control voltages or currents in the sensor 32 while the amplification part amplifies the analog signal from the chemical sensor 32. The potentiostat may then output the amplified analog signal to the analog-to-digital converter 34. The analog-to-digital converter 34 then converts the analog signal to a digital signal as described previously and outputs the digital signal to the microcontroller 36. The microcontroller 36 then estimates or computes a value of the concentration of the selected chemical.

FIG. 3 also illustrates an embodiment in which the sensor 32, the amplifier 38 and the analog-to-digital converter 34 all on the same integrated circuit die 30, and the microcontroller 36 is on a physically separate integrated circuit die 31. In this embodiment, the electrical data from the sensor 32 is converted to a digital signal in the analog-to-digital converter 34. After conversion to a digital signal 34, the signal is transmitted off of the die, through the appropriate terminals and wires and into the input terminals of a microcontroller 36 on a separate integrated circuit die 31. Such a connection of one die to another has the problems as described, in which noise may be introduced into the system at least three different locations. However, since the signal has been converted to a digital signal, the type of the signal is significantly more immune to noise than an analog signal traveling directly from the sensor 32 to a microcontroller. With a digital signal, the data being transmitted is a one or a zero, and therefore greater discrimination can be provided between the signal content and the noise content. Additionally, a digital signal may carry a large number of check bits, parity bits, or other type of error checking bits. In an 8-bit signal, two or three of the bits may be used as error correction code bits so that even if some noise is present in the coupling between the chip 30 and the chip 31, the microcontroller 36 can check the error correction bits contained in each byte and correct the errors to be assured that the data being received is the data that was sent. The ability to provide a large number of error correction bits across multiple bytes of data is a significant benefit with converting the data to a digital format prior to sending. In addition, the analog-to-digital converter 34 will often have a memory buffer so that the same data can be set in separate groups of bytes, separated from each other in time so that if the first set of bytes is subjected to noise, then a later second set of bytes set at a different time having the same data may avoid the same noise. In addition, repeatedly sending the same data in separate groups of bytes spaced in time permits the microcontroller 36 to compare the various sets of data with each other as part of the error correction code in order to be assured that the correct data has been received by the microcontroller 36. Thus, having an analog-to-digital converter 34 with a small buffer memory, whether it be SRAM registers, shift registers, or other small memories, is beneficial to achieve the purposes of sensing small quantities of the chemical to be sensed as previously described with respect to having all components on a single integrated circuit. Similarly, one or more parts of the microcontroller 36 may be on the same die as the analog-to-digital converter 34, and the sensor and other portions of it be on another die.

Figure 4:
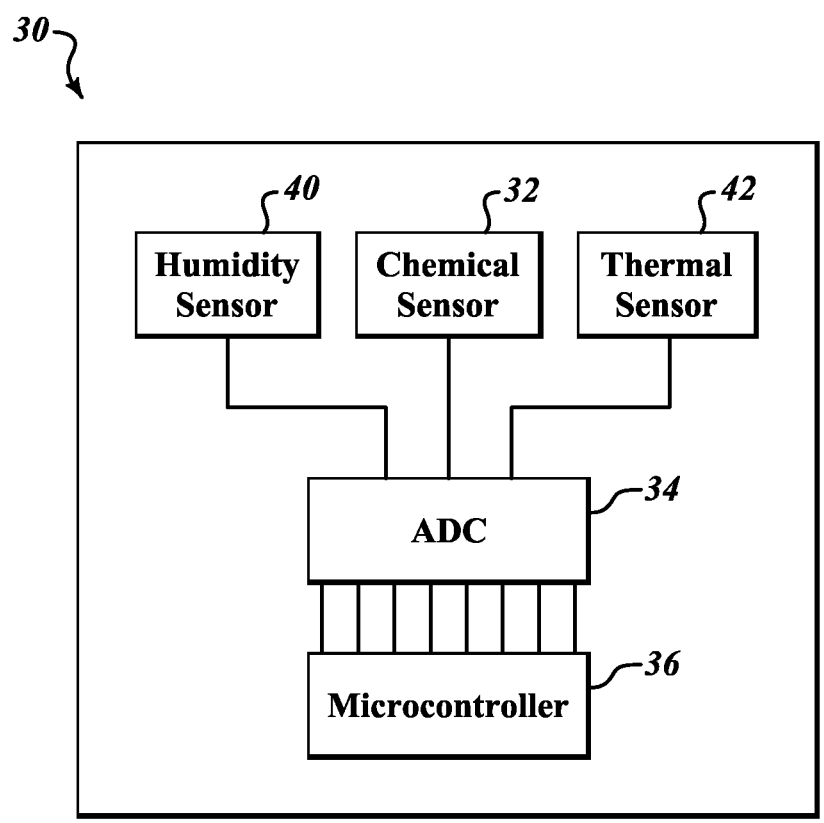
FIG. 4 is a block diagram of a semiconductor die including humidity and thermal sensors according to one embodiment.

FIG. 4 illustrates a semiconductor die 30 according to one embodiment. The semiconductor die 30 includes a chemical sensor 32, a humidity sensor 40, and a thermal sensor 42. The chemical sensor 32, the humidity sensor 40, and the thermal sensor 42 are each connected to the analog-to-digital converter 34. The analog-to-digital converter 34 is connected to the microcontroller 36 as described previously. The analog-to-digital converter 34 receives the analog signal from the chemical sensor 32 as described previously. The analog-to-digital converter 34 also receives a humidity signal from the humidity sensor 40 and a thermal signal from the thermal sensor 42.

The analog signal output by the chemical sensor 32 may be affected by humidity in the air or by the temperature of the air in the surrounding environment. Thus, the estimation or the computation of the value of the concentration of the selected chemical may be affected by the humidity or the temperature in the surrounding environment. For this reason, a humidity sensor 40 and a thermal sensor 42 may be included in the semiconductor die 30. The humidity sensor outputs a humidity signal indicative of the humidity in the surrounding environment. The thermal sensor 42 outputs a thermal signal indicative of the temperature of the surrounding environment. The analog-to-digital converter 34 may then convert the humidity signal and the thermal signal into respective digital signals. The analog-to-digital converter 34 then outputs the digital humidity signal and the digital thermal signal to the microcontroller 36. The microcontroller 36 then estimates or computes the value of the concentration of the selected chemical based in part on the analog signal from the chemical sensor, the humidity signal from the humidity sensor, and the thermal signal from the thermal sensor. The microcontroller 36 may reference calibration curves stored in memory and compare values stored in memory to the values of the digital signals output by the analog-to-digital converter 34. By comparing the values of the digital humidity signal, the digital chemical signal, and the digital thermal signal to the values stored in memory, the microcontroller 36 can estimate or compute a more accurate value of the concentration of the selected chemical. In the embodiment of FIG. 4, the analog-to-digital converter, similar to that in prior embodiments, may include a plurality of storage registers in order to store the different types of data being sensed for coordinating the sending of the data to the microcontroller. Thus, in each embodiment, it is possible to have one or more storage elements in the circuit prior to the microcontroller in order to store the sensed data.

Figure 5:
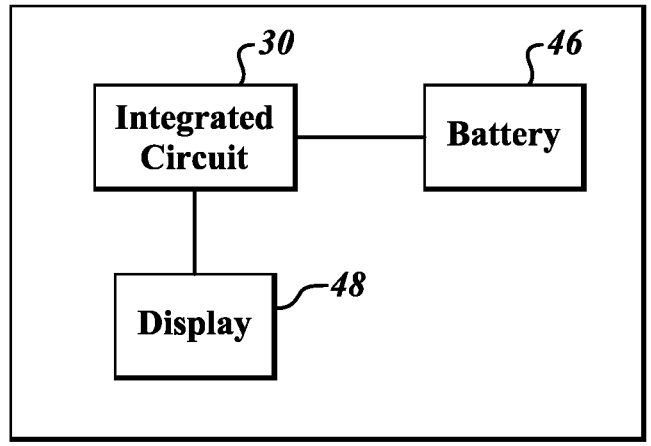
FIG. 5 is a block diagram of a chemical detection device according to one embodiment.

FIG. 5 illustrates a chemical detection device according to one embodiment. The chemical detection device 44 includes an integrated circuit 30, a battery 46, and a display 48. The battery supplies power to the integrated circuit 30. The battery also supplies power to the display 48. According to one embodiment, the integrated circuit 30 includes a chemical sensor 32 as described previously. The integrated circuit 30 also includes an analog-to-digital converter 34 and a microcontroller 36 as described previously. The chemical detection device is configured to detect the presence of a selected chemical. The chemical detection device 44 is also configured to display the concentration of the selected chemical. As described previously, the chemical sensor 32 on the integrated circuit 30 is configured to sense the presence of the selected chemical. The chemical sensor 32 then outputs an analog signal to the analog-to-digital converter 34. The analog-to-digital converter 34 then converts the analog signal to a digital signal. The analog-to-digital converter 34 then supplies the digital signal to the microcontroller 36. The microcontroller 36 then computes or estimates a value of the concentration of the selected chemical based on the digital signal. The microcontroller then outputs the value of the concentration of the selected chemical to the display 48. The display 48 then displays the value of the concentration of the selected chemical.

In one embodiment, the display 48 is a screen configured to display the concentration of the selected chemical. In one embodiment, display 48 includes a printer and a paper which displays the concentration of the selected chemical. The display 48 may be any one suitable that is for displaying the concentration of the selected chemical.

In one embodiment, the microcontroller 36 is configured to estimate or compute whether or not the value of the concentration of the selected chemical is above a selected threshold value. If the value of the concentration of the selected chemical is above the selected threshold, then the microcontroller 36 outputs a signal to the display 48 indicating that the concentration of the selected chemical has surpassed a selected threshold. The display 48 then indicates that the selected threshold has been surpassed. In one embodiment, the display 48 is an LED or a plurality of LEDs configured to provide a visual indication that the concentration has surpassed the threshold value. In one embodiment, the display 48 includes a red LED and a green LED. If the value of the concentration of the selected chemical has surpassed the threshold value, then the display 48 will illuminate the red LED. If the value of the concentration of the selected chemical has not surpassed the selected threshold, then the display 48 will illuminate the green LED. In one embodiment, the display 48 is an audio speaker which emits an audible sound indicating that the selected threshold has been surpassed. There are many possible implementations of the display 48 as will be apparent to those of skill in the art in light of the present disclosure.

In one embodiment, the chemical detection device 44 is configured to be installed on a wall of a house. The chemical detection device 44 may be configured to detect carbon monoxide, radon, smoke, or any other chemicals or elements. In one embodiment, the chemical detection device 44 is configured to be installed in or near the exhaust pipe of an automobile. The chemical detection device 44 detects the presence of a selected chemical or particulate. The chemical detection device 44 can be configured to detect any desired particulate in the exhaust system. The chemical detection device 44 can be configured to continuously monitor the concentration of the selected chemical or the chemical detection device 44 can be configured to perform a test on command. The chemical detection device 44 can be a reusable chemical detection device or a single use chemical detection device. In one embodiment, the chemical detection device 44 is a medical device, such as a blood glucose sensor, a cancer cell detector, a DNA or RNA detector, or any other suitable medical application.

Figure 6:
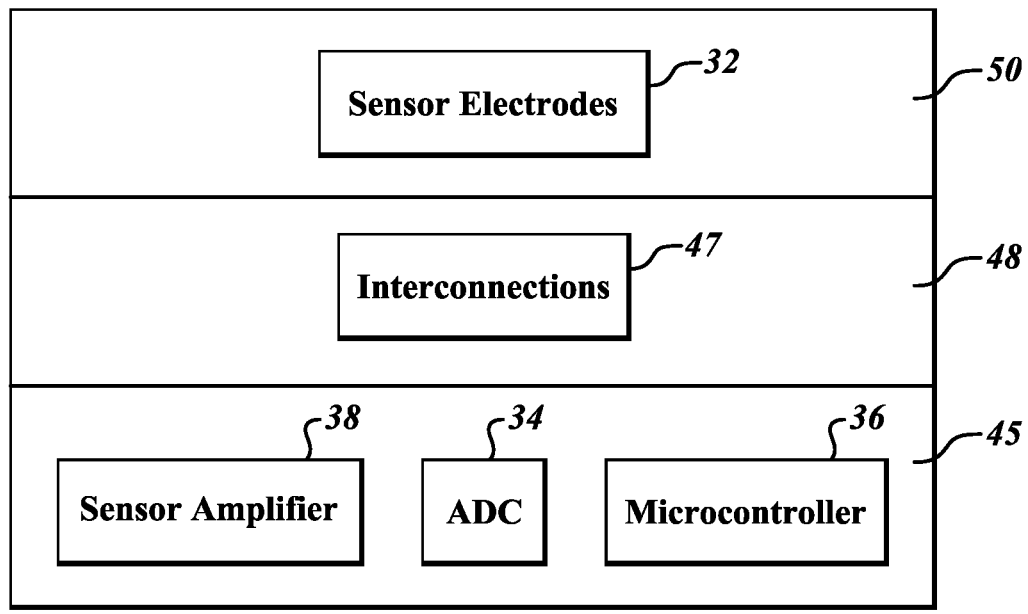
FIG. 6 is a cross section of a semiconductor die according to one embodiment.

FIG. 6 illustrates a simplified cross-section of a semiconductor die 30 according to one embodiment. The semiconductor die 30 includes a monocrystalline silicon layer 45. The monocrystalline silicon layer 45 includes the analog-to-digital converter 34, the microcontroller 36, and the sensor amplifier 38. The analog-to-digital converter 34, the sensor amplifier 38, and the microcontroller 36 comprise transistors formed in the monocrystalline silicon layer 45. The transistors that make up the microcontroller 36, the analog-to-digital converter 34, and the sensor amplifier 38 may be formed according to convention CMOS processes. The semiconductor die 30 includes a dielectric layer 48. The dielectric layer 48 may include silicon dioxide layers, nitride layers, spin-on glass layers, other planarizing layers, or any other dielectric layers as are well known to those of skill in the art. Metal interconnections 46 are formed in dielectric layer 48. The metal interconnections may be formed according to any suitable method including aluminum metal layers, tungsten plugs, titanium adhesion layers, or any other metal layers conventionally used to make vias, plugs, and metal tracks. The semiconductor die 30 includes a passivation layer 50. The passivation layer 50 may include phospho-silicate glass, oxynitrides, molding compounds, or combinations of these dielectric layers. Passivation layer 50 may also be formed of any other suitable passivation material. Sensor electrodes 32 are formed above the dielectric layer 48 and in the passivation layer 50. The sensor electrodes 32 comprise the chemical sensor 32 as described previously.

The sensor electrodes 32 may be formed on the dielectric layer 48. Metal interconnections 47 couple the sensor electrodes 32 to the sensor amplifier 38. The metal interconnections 46 also connect the sensor amplifier to the analog-to-digital converter 34. The interconnections 47 also connect the analog-to-digital converter 34 to the microcontroller 36. The metal interconnections 46 may also connect the microcontroller to contact pads (not shown). The sensor electrodes 32 are coated in an enzyme or reactant configured to react with the selected chemical. The enzyme or reactant is specifically selected to react with the selected chemical. Different reactants or enzymes may be used according to the particular selected chemical. In one embodiment, the passivation layer 50 is opened so that the electrodes 32 are exposed to the surrounding environment. The enzyme or reactant that coats the sensor electrodes 32 may then react with chemical sensors in the air or in a liquid placed on the semiconductor die 30 or in any other suitable manner. In one embodiment, the sensor amplifier 38 applies through the interconnections 47 a control signal to the sensor electrodes 32. The sensor amplifier 38 also receives an analog signal from the sensor electrodes 32 through the interconnections 47. The strength of the analog signal varies according to the presence of the selected chemical. In one embodiment, the analog signal is a current signal. As the selected chemical interacts with the reactant on the electrodes 32, the current level increases. In this way, the analog signal varies according to the concentration of the selected chemical. The sensor amplifier then amplifies the analog signal and supplies it to the analog-to-digital converter 34. The sensor amplifier 38 supplies the analog signal to the analog-to-digital converter 34 through the metal interconnections 46. The analog-to-digital converter 34 converts the analog signal to a digital signal as described previously. The analog-to-digital converter 34 then supplies the digital signal to the microcontroller 36 as described previously.

Figure 7:
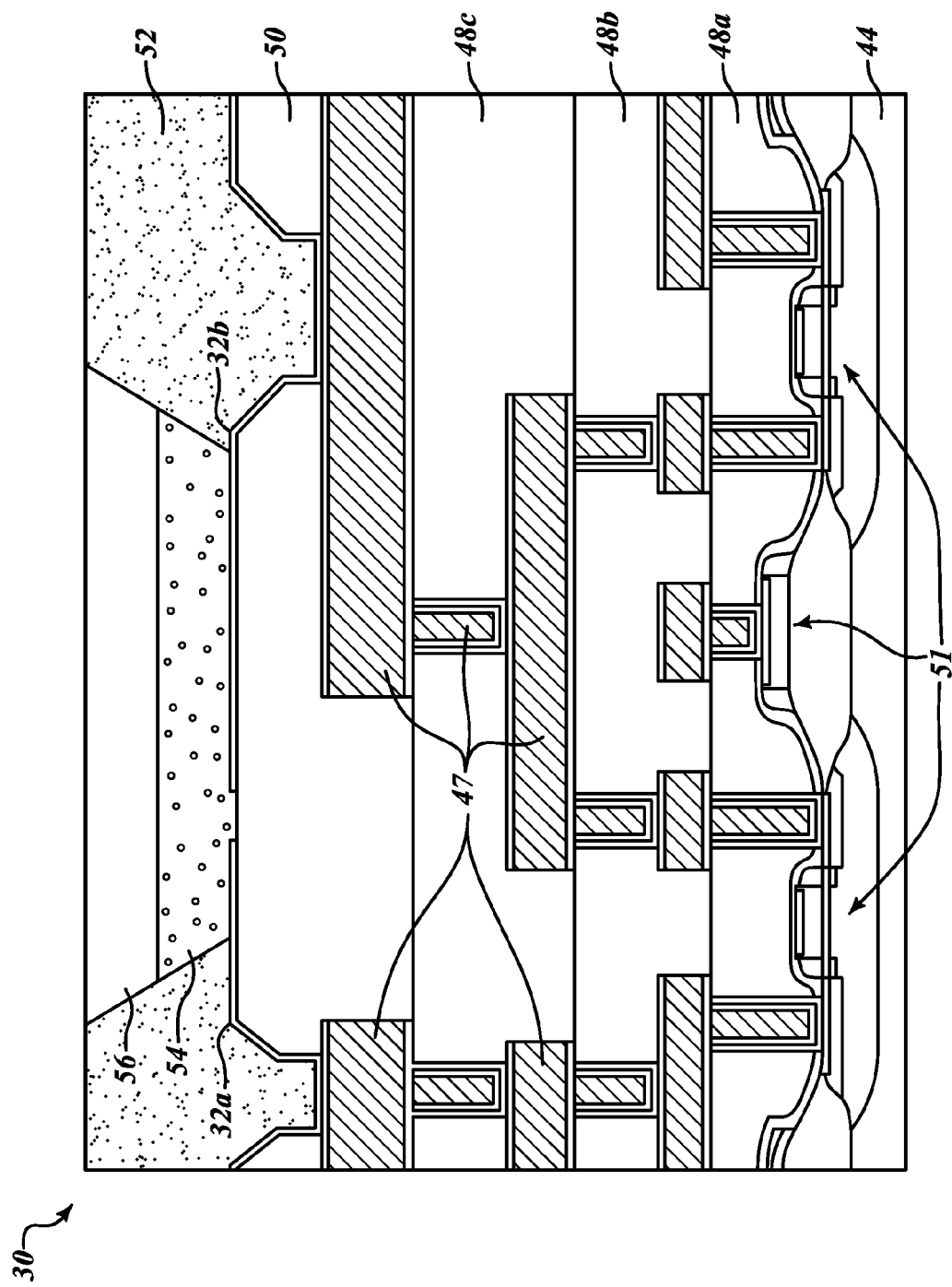
FIG. 7 is a cross section of a semiconductor die according to one embodiment.

FIG. 7 illustrates a cross-section of a semiconductor die 30 according to one embodiment. The semiconductor die 30 includes a monocrystalline silicon layer 44 as described previously. Transistors 51 are formed in the monocrystalline silicon layer 44. Transistors 51 may be formed according to any conventional processes as are well known to those of skill in the art. The semiconductor die 30 includes dielectric layers 48a, 48b, 48c. Metal interconnections 47 are formed in the dielectric layers 48a, 48b, 48c. The metal interconnections 47 include metal tracks, vias, and plugs. The metal tracks may be formed of an aluminum copper alloy, and may include titanium and titanium nitride adhesion and barrier layers as is known to those of skill in the art. The vias and plugs may be formed of tungsten and include adhesion and barrier layers of titanium and/or titanium nitride as described previously. The interconnections 46 may also be formed of any other suitable materials, as will be apparent to those of skill in the art in light of the present disclosure. The dielectric layers 48a, 48b, 48c may include silicon dioxide layers, silicon nitride layers, phosphosilicate glass layers, spin-on glass layers, other planarization layers, or any other suitable dielectric layers as are well known to those of skill in the art.

The semiconductor die 30 includes the passivation layer 50 formed on the dielectric layer 48c. The passivation layer 50 includes phosphosilicate glass layers, oxynitride layers, and other suitable passivation layers. Sensor electrodes 32a, 32b are formed on the passivation layer 50. The sensor electrodes 32a, 32b contact the metal interconnection layers 46. The metal interconnection layers connect the sensor electrodes 32a, 32b to the transistors 51. Transistors 51 form the sensor amplifier 38, the analog-to-digital converter 34, and the microcontroller 36. The semiconductor die 30 may include millions of transistors 51. The sensor electrodes 32a, 32b are covered in a molding compound 52. The molding compound includes an opening over portions of the electrodes 32a, 32b. A chemical reactant or enzyme 54 is deposited on the sensor electrodes 32a, 32b. An adhesive layer or a hardening layer 56 is placed on the reactant 54. In practice, the layer 56 may mix with the layer 54 and may anchor the anchor the layer 54 to the electrodes 32a, 32b, the passivation layer 50, and the molding compound 52.

Because the reactant is exposed to the surrounding environment, the reactant 54 may interact with a selective chemical in the environment. As the selected chemical interacts with the reactant 54, the reactant reacts to the selected chemical and an analog signal is sent from the electrodes 32a, 32b to the transistors 51. In particular, the analog signal is output to the sensor amplifier 38 as described previously. The sensor amplifier 38 amplifies the analog signal and outputs the analog signal to the analog-to-digital converter 34. The analog-to-digital converter 34 converts the analog signal to a digital signal and outputs the digital signal to the microcontroller 36. The microcontroller 36 then computes or estimates the value of the concentration of the selected chemical. The analog signal may vary according to the concentration of the selected chemical as described previously. In one embodiment, the selected chemical interacts with the reactant 54 and the reactant 54 reacts and generates free charge carriers. Free charge carriers may be individual electrons or ions or any other suitable free charge carrier. As more charge is available, the strength of the analog signal will increase. In one embodiment, the analog signal is a current signal flowing between electrodes 32a, 32b to the transistors 51. In one embodiment, the analog signal is a voltage signal. In one embodiment, the sensor electrodes include electrodes 32a, 32b. In one embodiment, the sensor electrodes include more than two electrodes. In one embodiment, the signal amplifier is a potentiostat 38. The chemical sensor 32 includes sensor electrodes 32a, 32b, 32c. Electrode 32c is not shown in FIG. 7. In one embodiment, the sensor electrodes 32a, 32b are formed of gold. In one embodiment, the sensor electrode 32a is formed of gold and the sensor electrode 32b is formed of platinum. Other suitable metals may be used for the sensor electrodes 32a, 32b as will be apparent to those of skill in the art in light of the present disclosure.

Figure 8:
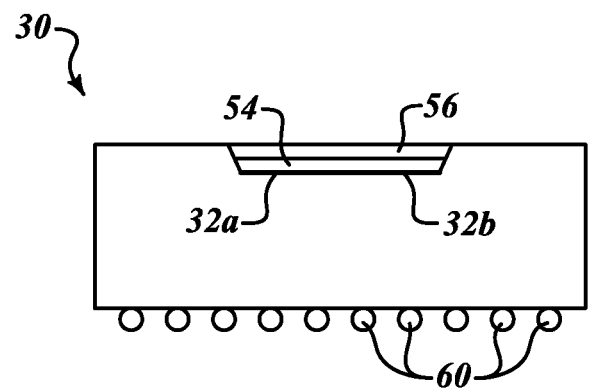
FIG. 8 is a cross section of a packaged semiconductor die and ball grid array according to one embodiment.

FIG. 8 illustrates a semiconductor die 30 according to one embodiment. FIG. 8 illustrates solder balls 60 on the bottom of the integrated circuit 30. The reactant 54 and the hardening layer 56 are also illustrated. The reactant 54 and the hardening layer 56 are exposed to the environment surrounding the semiconductor die 30. The semiconductor die 30 is covered in the molding compound. The solder balls 60 are connected to contact pads of the integrated circuit 30. Contact pads are not shown in FIG. 8 because they are covered by the molding compound. The contact pads would be connected to the solder balls 60 by through-hole vias or by implementing an embedded wafer level ball grid array as is known to those of skill in the art. The solder balls 60 allow the integrated circuit 30 to be connected in a chemical detection device 44 as described previously or connected in a chemical detection system configured to enable the detection of a selected chemical.

Figure 9:
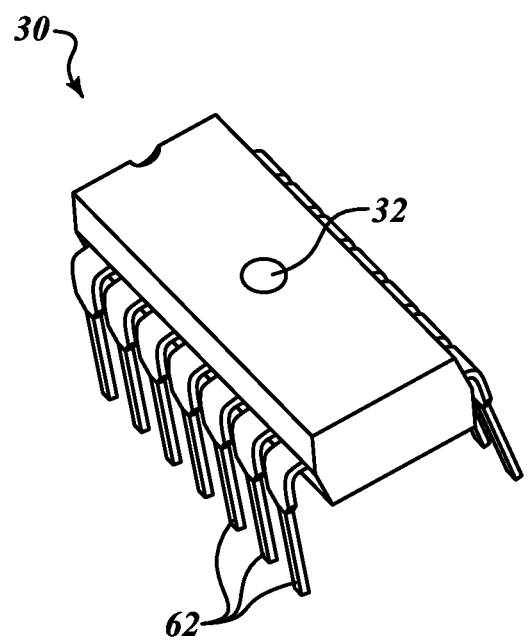
FIG. 9 is a cross section of a packaged semiconductor die and lead frame according to one embodiment.

FIG. 9 illustrates a semiconductor die 30 according to one embodiment. The semiconductor die 30 is packaged with a lead frame. The lead frame includes leads 62 protruding from the semiconductor die 30. A molding compound coats the semiconductor die 30. An opening in the molding compound exposes the hardening layer 56 and the reactant 54 of the chemical sensor 32 to the surrounding environment. In this way, the chemical sensor 32 can detect the presence of the selected chemical in the surrounding environment. The leads 62 allow the semiconductor die 30 to be installed in a chemical detection device 34 or in a chemical detection system. The semiconductor die 30 receives power through the leads 62. The microcontroller 36 of the semiconductor die 30 may also be programmed through the leads 62. Microcontroller 36 may output the value of the concentration of the selected chemicals through leads 62. The leads 62 may connect the semiconductor die 30 to a display 48 in order to display the value of the concentration of the selected chemical as described previously. Of course the semiconductor die 30 may be packaged in any suitable manner as will be apparent to those of skill in the art in light of the present disclosure. For example, a semiconductor die 30 may be packaged in a pin grid array, ball grid arrays, lead frames, embedded wafer level ball grid arrays, or any other suitable packaging method.

Figure 10:
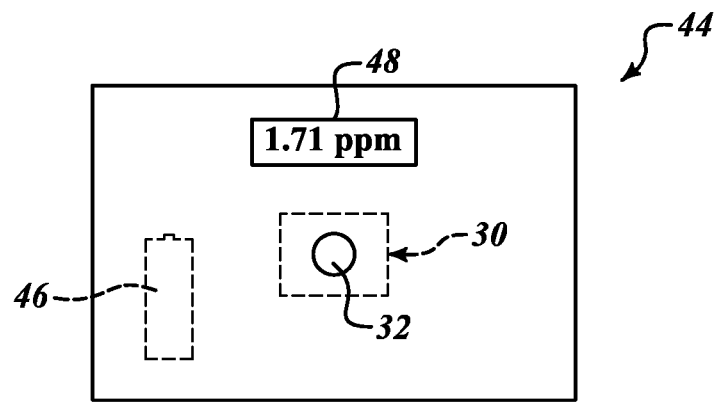
FIG. 10 is a chemical detection device according to one embodiment.

FIG. 10 illustrates a chemical detection device 44 according to one embodiment. Chemical detection device 44 includes a semiconductor die 30. The semiconductor die 30 includes a chemical sensor 32. The chemical sensor 32 is exposed to the surrounding environment through a hole in the chemical detection device 44. Chemical detection device 44 includes a battery 46 configured to supply power to the semiconductor die 30 and display 48. Display 48 is configured to display a value of the concentration of the selected chemical as described previously.

Figure 11:
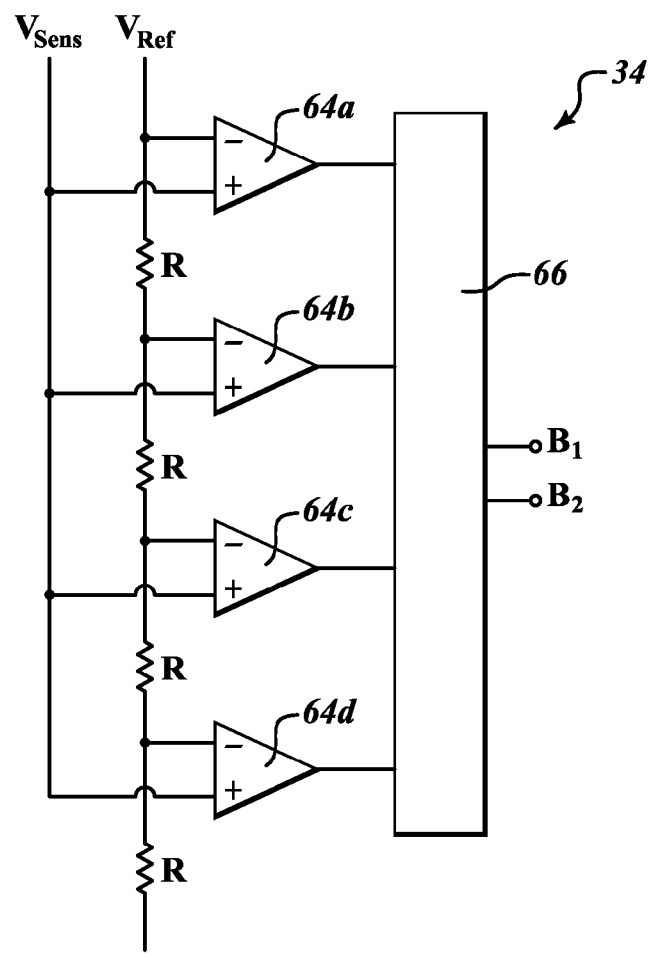
FIG. 11 is schematic diagram of an analog to digital converter according to one embodiment.

FIG. 11 is an analog to digital converter according to one embodiment. The analog to digital converter includes comparators 64a, 64b, 64c, and 64d. The analog to digital converter 34 further includes four resistors R connected in series. Each comparator 64a-d is connected to the analog signal Vsense on its non-inverting input. Each comparator The analog-to-digital converter 34 includes four comparators 64a, 64b, 64c, and 64d each receiving the midpoint voltage on a respective non-inverting node. A plurality of resistors R of equal value is connected in series between a reference voltage Vsense and $V_L$. The inverting inputs of the comparators 64a, 64b, 64c, and 64d are each connected to a respective node on the series chain of resistors R. The outputs of the comparators are each connected to a digital output encoder 66. The digital output encoder has two outputs B1, B2 each representing a respective bit of the digital output.

Each comparator 64a, 64b, 64c, 64d of the analog-to-digital converter 34 compares the analog voltage Vsense to a respective reference voltage. The respective reference voltages are divisions of the primary reference voltage Vref. The chain of resistors R thus acts as a voltage divider to provide a plurality of reference voltages. Each comparator 64a, 64b, 64c, 64d will output a high or low value according to the individual comparisons. The digital outputs B1 and B2 are determined by the comparisons. In particular the digital output encoder includes a plurality of logic gates configured to receive as four inputs the outputs of the comparators 64a, 64b, 64c, and 64d and to output two binary outputs B1 and B2 accordingly. The outputs B1, B2 can combine to make binary values 00, 01, 10, or 11.

The outputs B1 and B2 are read by the control circuitry of the microcontroller 36 and compared to values in memory. The analog-to-digital converter 34 of FIG. 11 illustrates only a two-bit analog-to-digital converter. In practice the analog-to-digital converter 34 may more than two bits, for example an 8 or 16 bit analog-to-digital converter. The threshold differences can be selected by selecting appropriate values of the resistors R connected in series. Many variations are possible as will be apparent to those of skill in the art in light of the present disclosure. All such embodiments fall within the scope of this disclosure.

Figure 12:
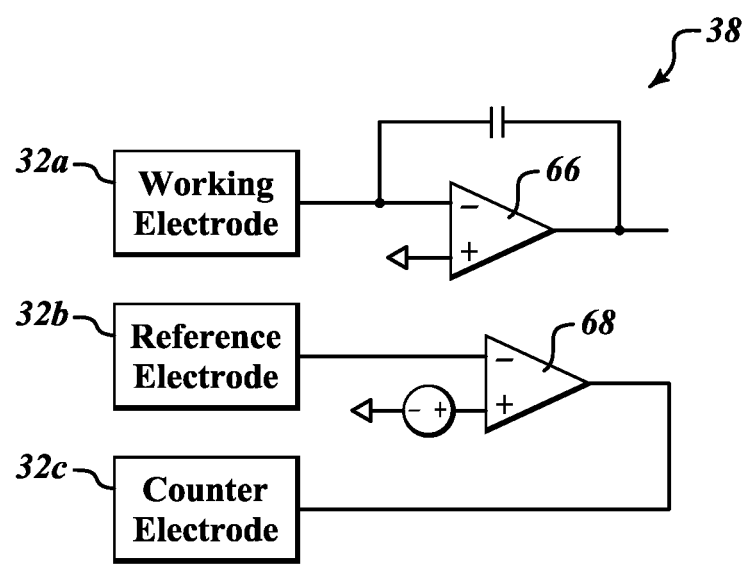
FIG. 12 is a schematic diagram of potentiostat and chemical sensor according to one embodiment.

FIG. 12 illustrates a potentiostat 38 according to one embodiment. The potentiostat 38 has a current integrator 68 and a control amplifier 70. FIG. 13 illustrates electrodes 32a, 32b, and 32c. The working electrode 32a is coupled to the inverting input of the current integrator. The inverting input of the control amplifier is connected to the reference electrode 32b of the chemical sensor 32. The output of the control amplifier 70 is coupled to the counter electrode 44c of the chemical sensor. The current integrator 68 outputs an analog signal representative of the concentration of the selected chemical. The control amplifier 70 ensures that the voltage on electrodes 32a, 32b is held at a selected value.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device comprising:
a semiconductor die;
a chemical sensor on the semiconductor die, the chemical sensor configured to output a first analog signal indicative of a presence of a selected chemical;
a humidity sensor on the semiconductor die, the humidity sensor configured to output a second analog signal indicative of humidity in a surrounding environment;
an analog to digital converter on the semiconductor die and coupled to the chemical sensor and the humidity sensor, the analog to digital converter configured to receive the first analog signal and to convert the first analog signal to a first digital signal representative of the concentration of the selected chemical and configured to receive the second analog signal and convert the second analog signal to a second digital signal representative of the humidity in the surrounding environment; and
a microcontroller on the semiconductor die and coupled to the chemical sensor, the microcontroller configured to receive the first and the second digital signals and to compute a concentration of the selected chemical based on the first and the second digital signals.

2. The device of claim 1 further comprising a signal amplifier on the semiconductor die, the signal amplifier configured to receive the first analog signal from the chemical sensor, to amplify the first analog signal, and to output the first analog signal to the analog to digital converter.

3. The device of claim 2 wherein the amplifier is a potentiostat.

4. The device of claim 3 wherein the chemical sensor includes a working electrode and a reference electrode each coupled to the potentiostat, the potentiostat being configured to control a voltage supplied to the chemical sensor.

5. The device of claim 1 further comprising:
a battery coupled to the semiconductor die and configured to supply power to the semiconductor die; and
a display coupled to the semiconductor die, the display configured to display the output signal.

6. The device of claim 5 comprising a casing that houses the semiconductor die and the battery, the casing being configured to allow removal and replacement of the semiconductor die.

7. The device of claim 1 comprising a passivation layer covering the semiconductor die, the passivation layer having an opening that exposes a portion of the chemical sensor.

8. A semiconductor die comprising:
a first sensor configured to detect a presence of a selected chemical and to output a first signal representative of the presence of the selected chemical;
an amplifier coupled to the first sensor and configured to receive the first signal and to output an amplified second signal;
a second sensor configured to detect humidity in a surrounding environment and to output a third signal representative of the humidity in the surrounding environment;
an analog to digital converter coupled to the amplifier, the analog to digital converter configured to receive the second signal and to convert the second signal to a first digital signal and to receive the third signal and to convert the third signal to a second digital signal; and
a microcontroller coupled to the analog to digital converter, the microcontroller being configured to output a first signal indicative of the presence of the selected chemical based on the first and the second digital signals.

9. The semiconductor die of claim 8 wherein the amplifier is a potentiostat.

10. The semiconductor die of claim 8 further comprising a temperature sensor configured to output temperature signal.

11. The semiconductor die of claim 10 wherein the microcontroller computes the concentration of the selected chemical based in part on the temperature signal.

12. The semiconductor die of claim 8 wherein the amplifier, the analog to digital converter, and the microcontroller are formed in a monocrystalline semiconductor substrate of the semiconductor die.

13. The semiconductor die of claim 12 comprising metal interconnections between the semiconductor substrate and the chemical sensor.

\* \* \* \* \*